United States Patent
Donitzky et al.

(10) Patent No.: US 10,624,787 B2
(45) Date of Patent: Apr. 21, 2020

(54) APPARATUS FOR CUTTING A TISSUE SECTION OF AN EYE BY LASER RADIATION

(75) Inventors: Christof Donitzky, Eckental (DE);
Thomas Deisinger, Zirndorf (DE);
Bernd Zerl, Uttenreuth (DE)

(73) Assignee: Alcon Inc. (CH)

( * ) Notice: Subject to any disclaimer, the term of this patent is extended or adjusted under 35 U.S.C. 154(b) by 1835 days.

(21) Appl. No.: 12/501,124

(22) Filed: Jul. 10, 2009

(65) Prior Publication Data
US 2011/0009851 A1   Jan. 13, 2011

(51) Int. Cl.
*A61F 9/009*   (2006.01)
*A61F 9/008*   (2006.01)

(52) U.S. Cl.
CPC .......... *A61F 9/009* (2013.01); *A61F 9/00825* (2013.01); *A61F 2009/00872* (2013.01)

(58) Field of Classification Search
CPC .................. A61F 9/00825; A61F 9/009; A61F 2009/00872; A61F 9/008–2009/00897
USPC .............................................. 606/10–12, 4–6
See application file for complete search history.

(56) References Cited

U.S. PATENT DOCUMENTS

| | | | |
|---|---|---|---|
| 3,982,539 A * | 9/1976 | Muriot | 604/120 |
| 4,546,773 A | 10/1985 | Frederic et al. | |
| 5,549,632 A | 8/1996 | Lai | |
| 5,591,185 A * | 1/1997 | Kilmer | A61F 9/013 606/161 |
| 6,126,668 A | 3/2000 | Bair et al. | |
| 7,390,089 B2 * | 6/2008 | Loesel et al. | 606/11 |
| 8,475,433 B2 * | 7/2013 | Mrochen | A61F 9/009 606/5 |
| 2004/0243112 A1 | 12/2004 | Bendett et al. | |
| 2005/0192562 A1 | 9/2005 | Loesel et al. | |

(Continued)

FOREIGN PATENT DOCUMENTS

| | | |
|---|---|---|
| DE | 10354025 | 6/2005 |
| EP | 0327693 | 8/1989 |

(Continued)

OTHER PUBLICATIONS

PCT International Search Report for PCT/EP2008/006962, dated Apr. 27, 2009, 6 pages.

(Continued)

*Primary Examiner* — Gary Jackson
*Assistant Examiner* — Jonathan Kuo
(74) *Attorney, Agent, or Firm* — Kenneth Bassinger, Esq.

(57) ABSTRACT

An apparatus for cutting a tissue part of an eye by means of laser radiation includes a suction-ring unit (16) which is capable of being mounted onto the eye, with a ring axis (22), a mechanical interface unit (34) which is separate from the suction-ring unit (16), which is capable of being moved along the ring axis (22) in coupling contact with the latter, and which is capable of being mechanically coupled with optical means (70) which focus the laser radiation onto or into the tissue part (12) of the eye, and sealing means (44, 52) which upon movement of the interface unit (34) in coupling contact with the suction-ring unit (16) form a space (58) which is capable of being evacuated and which is delimited by sealing surfaces (46, 60) of the interface unit (34) and of the suction-ring unit (16) and of the sealing means (44, 52).

9 Claims, 2 Drawing Sheets

(56) References Cited

U.S. PATENT DOCUMENTS

Figure 1A:
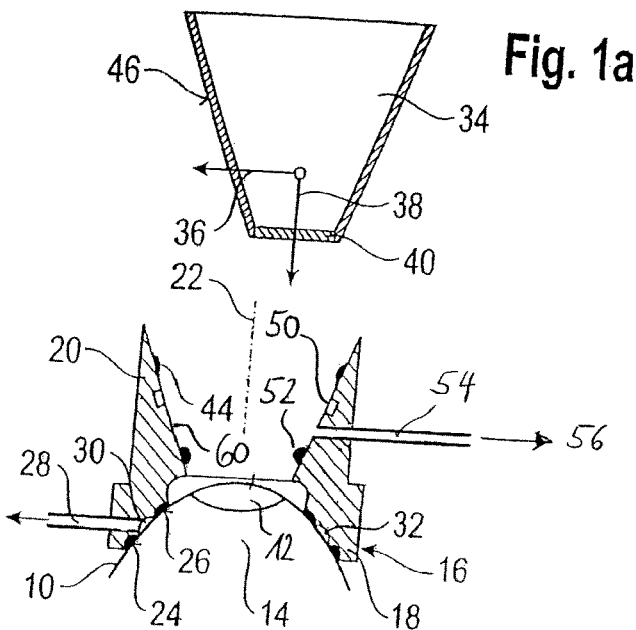

| | | | |
|---|---|---|---|
| 2007/0093795 A1 | 4/2007 | Melcher et al. | |
| 2007/0237620 A1 | 10/2007 | Muhlhoff et al. | |
| 2008/0071254 A1 | 3/2008 | Lummis et al. | |
| 2010/0241108 A1* | 9/2010 | Wullner | A61F 9/008 606/5 |

FOREIGN PATENT DOCUMENTS

| | | | | |
|---|---|---|---|---|
| EP | 199055 | | 4/2002 | |
| EP | 1570822 | | 9/2005 | |
| EP | 1970034 | | 3/2007 | |
| JP | 4194858 B2 | | 12/2008 | |
| WO | WO-2003002008 | | 1/2003 | |
| WO | WO-2004096106 | | 11/2004 | |
| WO | WO2005039462 A1 | | 5/2005 | |
| WO | WO-2005048895 | | 6/2005 | |
| WO | WO-2006/090217 | | 8/2006 | |
| WO | WO-2006121066 | | 11/2006 | |
| WO | WO 2008/110368 | * | 9/2008 | A61F 9/013 |
| WO | WO 2010/022745 | * | 3/2010 | 606/10 |
| WO | WO-2010/022745 | | 3/2010 | |

OTHER PUBLICATIONS

EP International Search Report for EP1970034, dated Aug. 23, 2007, 4 pages.

* cited by examiner

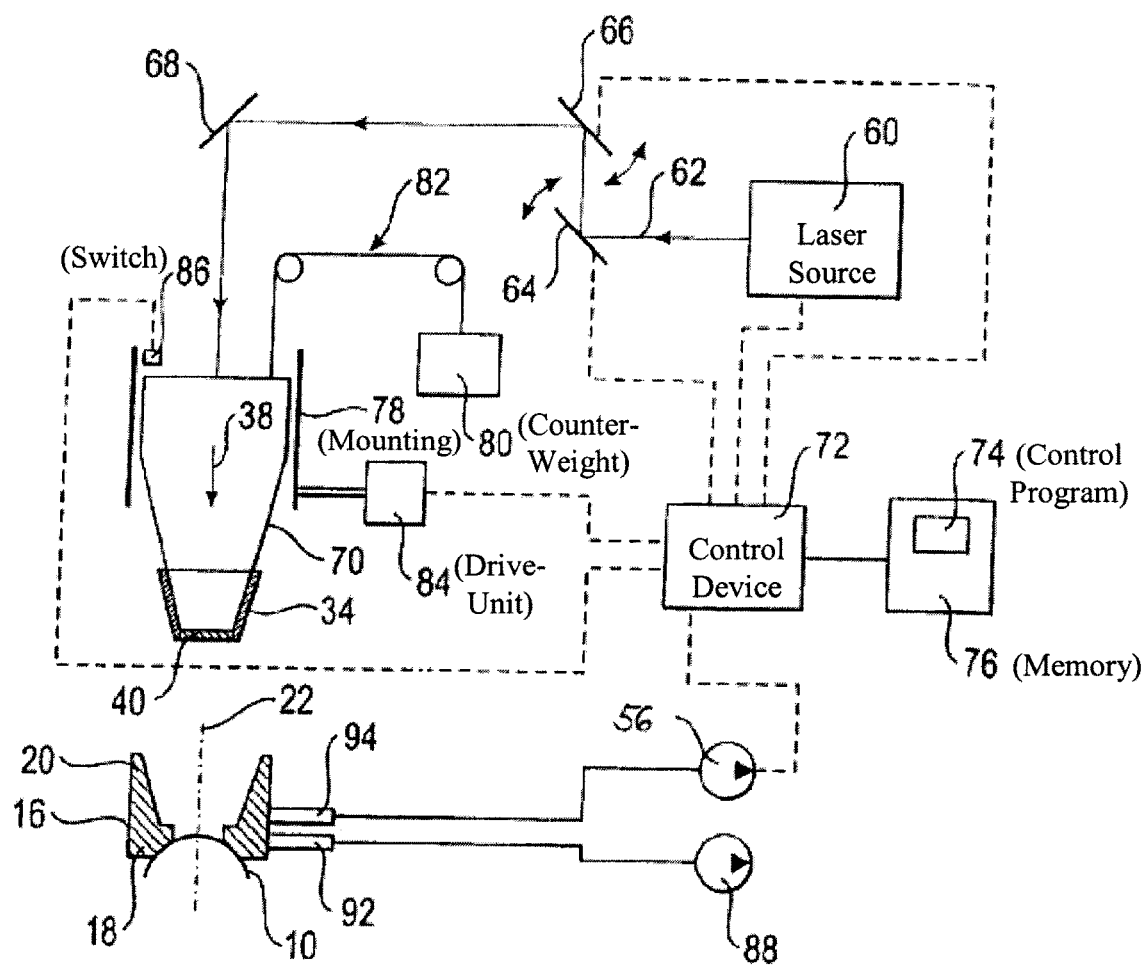

APPARATUS FOR CUTTING A TISSUE SECTION OF AN EYE BY LASER RADIATION

The invention relates to an apparatus for cutting a tissue part of an eye, having the features of the precharacterising portion of claim 1. Such an apparatus is known from PCT/EP2008/006962.

The invention is concerned generally with the establishment of a mechanical coupling between a biological tissue and a laser device, the laser radiation of which is utilised for the purpose of treating the tissue. In particular, the invention is concerned with the coupling of a laser device to an eye, in particular a human eye, in order to introduce one or more incisions into the eye with the laser radiation.

For a targeted action of the laser radiation a precise localisation of the beam focus relative to the tissue to be treated is indispensable. In particular for the generation of incisions in the tissue, frequently a relatively small beam focus is striven for, in order to keep the thickness of the incision small. The positioning of the beam focus then also has to be correspondingly precise. This holds, in particular, for the introduction of incisions into ocular tissue, such as occur, for example, within the scope of so-called fs LASIK. LASIK stands for laser in-situ keratomileusis and designates a technique for treating eyesight defects, in which firstly a covering disc (in specialist circles normally designated as a flap) is cut out of the anterior region of the cornea, which in part still remains connected to the cornea so that it can be folded aside for a subsequent ablation of underlying corneal tissue by means of laser radiation. After implementation of the ablation (resection of tissue), the flap is folded back, and a relatively rapid healing takes place, with the corneal surface largely undamaged.

For the production of the flap, a previously common technique uses a mechanical planer (microkeratome) which cuts into the cornea from the side with a rapidly oscillating cutting blade. Work has also been proceeding for some time on systems that permit generation of a flap by means of focused laser radiation with pulse durations within the femtosecond range. Hence the name femtosecond LASIK or fs LASIK. The radiation in this case is focused beneath the anterior surface of the cornea in the interior of the tissue, and the focal points are positioned in the desired surface in such a way that, as a result, a flap is cut out of the cornea.

But tissue incisions in the eye are needed not only in fs LASIK but also in other indications, for instance in keratoplasty (e.g. anterior or posterior lamellar keratoplasty, penetrating keratoplasty in corneal graftings), in fs lenticle extraction for the purpose of refraction correction, in the cutting of intercorneal ring segments for the purpose of stabilising keratoconus and protrusion of the cornea (e.g. for the insertion of intacs, i.e. small implanted ring segments for biomechanical stabilisation of the cornea), in cataract incisions, in presbyopia incisions in the crystalline lens, in intrastromal inlays, in keratotomy for astigmatisms, in corneal resection and such like.

In the state of the art it is known (see e.g. U.S. Pat. No. 5,549,632, WO 03/002008 A1) in the case of eye-laser devices to impress a plane-parallel applanation lens onto the cornea. As a result of the impressing of the applanation lens, the eye is deformed and conforms two-dimensionally to the underside of the applanation lens facing towards the eye. The beam focus of the laser radiation is referenced in the z-direction in relation to the applanation lens (the z-direction in this connection means the longitudinal direction of the beam). By virtue of the abutting of the eye against the applanation lens, there is a fixed z-reference between eye and lens, permitting a precise z-positioning of the beam focus in arbitrary regions in the cornea or in other tissue structures deep within the eye.

Besides plane-parallel applanation lenses, lenses (or generally contact glasses) have also become known in the state of the art having spherically, aspherically or otherwise curved surfaces, which equally enable a z-referencing. By virtue of suitably concave design of the underside of the lens facing towards the eye, the deformation of the eye in the course of mounting the lens can be reduced. This is advantageous to the extent that the intraocular pressure does not increase so much as in the case of an impressed applanation lens having a flat underside. However, the curved lens surfaces impair the focusability of the laser radiation.

In order to keep the eye of the patient at a fixed distance from the focusing optics of the laser device, in the state of the art use is made, as a rule, of suction rings which are aspirated onto the sclera of the eye by means of partial vacuum and surround the cornea in the form of a ring. Either the applanation lens in this case is integrated into the suction ring—as shown, for example, in FIG. 4C of the aforementioned U.S. Pat. No. 5,549,632—or the applanation lens is part of a separate component which is coupled with the suction ring; see, for example, FIG. 7 of WO 03/002008 A1, where the applanation lens is permanently fitted to a conical body which in the region of its cone base is constructed for coupling to the focusing optics of a laser device and at its narrow cone end can be brought into firm coupling with the suction ring by means of a separate compression forceps.

The tripartite structural design according to WO 03/002008 A1—with a suction ring, a compression forceps and a conical body bearing the applanation lens—permits a mutually independent guidance of the treatment optics of the laser device and of the eye of the patient right up close to one another. The suction ring in this case is already seated on the eye, whereas the cone is already fitted to the treatment optics. Once the treatment optics and the eye of the patient have been brought close enough to one another, the compression forceps, which establishes the mechanical coupling between the cone and the suction ring, comes into operation.

It is readily comprehensible that the mechanical fixation of the eye in relation to the treatment optics by means of the compression forceps is a critical phase of the surgical preparation. The compressive forces and shear forces acting in this process must not result in injuries to the eye of the patient or bring about an excessive and possibly dangerous increase in the intraocular pressure as a result of imprecise positioning of the mechanical components involved relative to one another. If an increased intraocular pressure occurs over a relatively long period, under certain circumstances this may result in damage to the optic nerve. Even if it is possible to position the optics more or less precisely by means of a joystick, the cone is nevertheless rigidly connected to the optics, for which reason the mechanical contact finally brought about with the eye and the associated levelling of the eye remain rigid. The forces exerted on the eye in this connection—specifically, both the forces arising during the procedure of coupling and the forces acting after applanation has taken place—are hardly predictable and may be different from patient to patient.

Overall, for numerous solutions known in the state of the art it is characteristic that an applanation lens—or, expressed more generally, a contact glass, no matter of what shape—is impressed onto the eye in the course of the coupling of the eye to the treatment optics, specifically so strongly that the eye conforms to the contact glass in the region required for the following treatment. This impressing of the contact glass onto the eye is normally associated with pressure surges which may be felt to be unpleasant by the patient. The eye is squeezed in the process and under certain circumstances may suffer damage, particularly because the tensile, compressive and shear forces arising cannot be precisely defined in advance.

The object underlying the invention is to configure an apparatus of the type mentioned in the introduction in such a way that an optimal coupling of the eye of a patient to the optics of the laser system is promoted. Undesirable loads on the eye—such as, in particular, tissue indentations or injuries to the epithelium—are to be prevented.

For this purpose, the invention provides an apparatus for cutting a tissue part of an eye by means of focused laser radiation, said apparatus including the following elements:
  a suction-ring unit which is capable of being placed onto the eye, with a ring axis,
  a mechanical interface unit which is separate from the suction-ring unit, which is capable of being moved along the ring axis in coupling contact with the latter, and which is capable of being mechanically coupled with optical means which focus the laser radiation onto or into the tissue part of the eye, and
  sealing means which upon movement of the interface unit in coupling contact with the suction-ring unit form a space which is capable of being evacuated and which is delimited by sealing surfaces of the interface unit and of the suction-ring unit and of the sealing means.

In accordance with the invention the aforementioned space which is capable of being evacuated is accordingly exclusively delimited by mechanical components of the apparatus itself and not by parts of the eye. This means that the fixation of the interface unit directly to the cornea by vacuum, which is still provided in many cases in the state of the art, does not take place in accordance with the invention, but rather in a first step of the coupling only the mechanical components constituted by 'interface unit' and 'suction-ring unit' are firmly coupled mechanically with one another, specifically by generation of a vacuum in the aforementioned space which is capable of being evacuated and which is exclusively delimited by surfaces that pertain either to the interface unit or to the suction-ring unit but not to the eye.

According to a preferred configuration, the sealing surfaces of the suction-ring unit and the sealing surfaces of the interface unit, which are complementary to the sealing surfaces of the suction-ring unit, are each frustoconical (conical).

In the decoupled state—that is to say, in a state in which the suction-ring unit is still remote from the interface unit—the sealing means may be provided on the suction-ring unit and/or on the interface unit.

The sealing means are preferably each annular and made of elastic material. It is also possible to generate the seal in self-sealing manner by means of a mechanical snug fit.

Figure 1B:
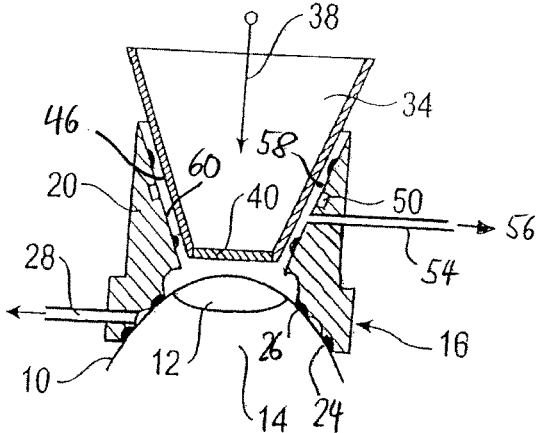
Figure 1C:
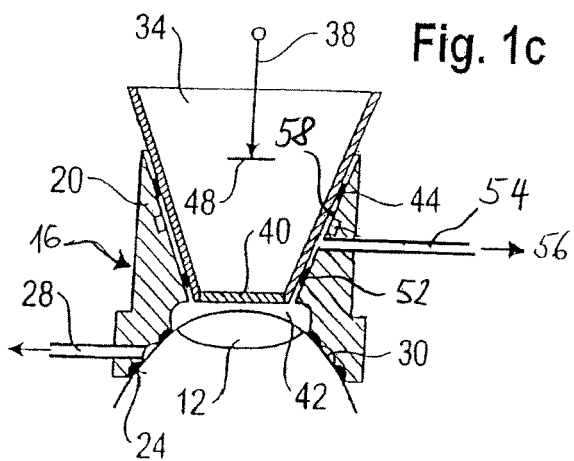

An exemplary embodiment of the invention will be described in more detail in the following on the basis of the drawing. Represented are:

FIGS. 1a-1c: schematically, consecutive phases in the course of the coupling of an interface unit to a suction-ring unit seated on an eye; and FIG. 2: in schematised manner, an exemplary embodiment of a laser device for cutting a tissue part of an eye.

In the exemplary embodiment shown in FIGS. 1a-1c the (human) eye to be treated is denoted by 10. The cornea of the eye 10 is shown at 12, whereas the sclera is denoted by 14.

One or more incisions are to be introduced into the cornea 12 of the eye 10 by means of pulsed laser radiation with pulse durations within the femtosecond range. The laser radiation necessary for this is provided by a laser source which is not represented in any detail. For example, the wavelength of the treatment radiation beamed into the eye 10 lies in the near-infrared region. For example, use may be made of an Yb laser radiating at 1030 nm.

Before a start is made with the laser treatment of the eye, the eye 10 firstly has to be coupled to the laser device equipped with the laser source, in order to be able to position the beam focus precisely in the cornea in the so-called z-direction (radiation direction). For this purpose, firstly a suction-ring unit 16 is placed onto the eye 10 in a manner known as such and is fixed to the eye 10 by partial vacuum. The suction-ring unit 16 stabilises and fixes the eye 10. It exhibits a lower part 18, forming the actual suction ring 18, an insertion funnel 20, connected to the lower part 18 and produced integrally with the latter, and also a ring axis 22. The lower part 18 forms two full-perimeter sealing surfaces 24, 26 in the form of a ring, each intended for abutment against the sclera 14, which bound between themselves a full-perimeter suction chamber 30 in the form of a ring, connected to an evacuation channel 28. The sealing surfaces 24, 26 may, for example, each be formed by a separate sealing element fitted to the lower part 18. For the purpose of forming the suction chamber 30, on the inner-periphery shell of the lower part 18 facing towards the eye a corresponding annular groove—denoted by 32—is formed. The suction chamber 30 is bounded exclusively between the suction-ring unit 16 and the sclera 14. As a result of evacuation of the suction chamber 30, the suction-ring unit 16 is firmly attached to the eye 10 by suction. For this purpose, the evacuation channel 28 is connected to a source of partial vacuum, not represented in any detail, in the form of an evacuation pump.

A mechanical companion part to the suction-ring unit 16 which is fixed on the eye 10 in such a way is an interface unit, generally denoted by 34, which, in a manner not represented in any detail, is capable of being firmly but releasably coupled with focusing optics of the aforementioned laser device. The interface unit 34 is capable of being displaced, together with the focusing optics, relative to the patient and to the suction-ring unit 16 fastened to him/her along a horizontal direction indicated by a horizontal arrow 36 and along a vertical direction indicated by a vertical arrow 38. The capacity for displacement of the interface unit 34 may be brought about at least partly by motorised means, for example by means of an electromotive drive. An at least partly manual capacity for movement of the interface unit 34 relative to the suction-ring unit 16 is also conceivable.

Overall, the interface unit 34 is of frustoconical design, being formed at its wider cone end (at the top in FIGS. 1a-1c) for coupling with the focusing optics, and bearing at its narrower cone end a contact glass 40 taking the form, in the exemplary case that is shown, of a plane-parallel applanation lens.

In a first phase of the procedure for coupling the eye 10 to the laser device the interface unit 34 is moved relative to the suction-ring unit 16 in the arrow direction 36 into a position in which it is located coaxially above the insertion funnel 20, so that the interface unit 34 can subsequently enter the insertion funnel 20 by being axially lowered. The phase of the entering of the interface unit 34 into the insertion funnel 20 of the suction-ring unit 16 is represented in FIG. 1b. In the course of the lowering of the interface unit 34, the applanation lens 40 approaches the eye 10; at the same time, the radial air gap between the insertion funnel 20 and the interface unit 34 becomes smaller. The conically extending inner-periphery shell 60 of the insertion funnel 20 and the equally conically extending, i.e. in complementary manner, outer-periphery shell 46 of the interface unit 34 bear or form in each case sealing means 44, 52.

The sealing means that are effective between the suction-ring unit 16 and the interface unit 34 are, in the exemplary case that is shown, formed by a ring seal 44 fitted to the insertion funnel 20 and by the part of the outer-periphery shell of the interface unit 34 situated opposite this ring seal 44 in the entered state. This part of the outer-periphery shell of the interface unit 34 acting as a sealing surface is denoted by 46 in FIG. 1a. The ring seal 44 may, for example, be a lip seal or an O-ring. It will be understood that alternatively such a ring seal may be provided on the interface unit 34. It is furthermore conceivable to dispense with a separate sealing element, provided that the outer surface of the interface unit 34 and the inner surface of the insertion funnel 20 are sufficiently smooth and come to be located alongside one another sufficiently closely.

In a manner analogous to the ring seal 44, a further ring seal 52 is arranged in offset manner on the suction-ring unit 16 in the direction towards the eye. For the further ring seal 52, what was stated above with respect to ring seal 44 with regard to configuration and its arrangement on the suction-ring unit or on the interface unit 34 applies correspondingly.

When the interface unit 34 is coupled to the suction-ring unit 16 the two ring seals 44, 52 described above form a space 58, cf. FIGS. 1b and 1c. The space 58 is bounded vertically at the top and bottom by the seals 44 and 52 and on both horizontal sides, on the one hand by an outer surface of the interface unit 34 as sealing surface 46, and on the other hand by an outer surface 60 of the insertion funnel 20 of the suction-ring unit 16 as sealing surface 60. The space 58 is accordingly exclusively delimited by the aforementioned elements and has no contact at any point with a component of the eye 10. In particular, no air-conducting connection exists between the interior of the space 58 and a surface of the eye 10.

According to FIG. 1b the interface unit 34 is lowered vertically—i.e. downwards in the Figures—in at least approximately coaxial position in relation to the suction-ring unit 16. In the process, the positions of suction-ring unit 16 and interface unit 34 adapt themselves to one another of their own accord by reason of the floating bearing of the latter (see below).

The lowering of the interface unit in the arrow direction 38 (corresponding to the axial direction of the suction-ring unit 16) stops at a predetermined axial relative position of the two units, in which the space 58 is closed off in sufficiently airtight manner in order to evacuate it via an evacuation channel 54 by means of a pump 56 (not shown) and in this way to couple the interface unit 34 firmly to the suction-ring unit 16. This state is shown in FIG. 1c. In order to detect the end position and hence to conclude the lowering, a sensor may be arranged at a suitable point. For example, a sensor 50 may have been positioned at the point specified in the Figures. It is also possible to arrange a sensor on the focusing optics 70 (FIG. 2). It is also possible to provide a mechanical limit switch 86 (FIG. 2). The sensor 50 is suitably positioned in order to emit an appropriate sensor signal when the relative position between interface unit and suction-ring unit has attained a predetermined spacing of the two units.

FIG. 2 shows schematically components of an apparatus for cutting a tissue part of an eye by means of laser radiation, wherein the coupling previously described on the basis of FIGS. 1a-1c between a suction-ring unit and an interface unit can be employed. Components that are identical to, or that act identically to, those in FIGS. 1a-1c are denoted in this case by identical reference symbols. With a view to avoiding repetition, reference is made to the preceding remarks relating to these components.

The laser device according to FIG. 2 includes a laser source 60 for pulsed laser radiation with pulse durations within the femtosecond range. The laser beam—denoted by 62—emitted by the laser source 60 reaches, via a deflecting device (scanner) formed here by two controllable deflecting mirrors 64, 66, a deviating mirror 68, from which the laser beam 62 reaches focusing optics 70. At the distal end, i.e. the end close to the eye, of the focusing optics 70 the interface unit 34 is releasably coupled. The deflecting mirrors 64, 66 are each arranged so as to be tiltable and permit a deflection of the laser beam 62 in an x-y plane which is normal to the longitudinal direction of the beam (z-direction). They are controlled by an electronic control device 72 in accordance with an incision profile given by the shape and position of the desired incision. The incision profile is embodied in a control program 74 which is saved in a memory 76 which can be accessed by the control device 72. For the purpose of z-relocation of the beam focus, either the focusing optics 70 or at least one lens contained therein may be adjustable in the longitudinal direction of the beam, under the control of the control device 72. Alternatively it is possible to arrange a lens of beam-expanding optics, not represented in any detail in FIG. 2, arranged between the laser source 60 and the deflecting mirrors 64, 66 so as to be relocatable in the longitudinal direction of the beam, in particular an input-side diverging lens of such beam-expanding optics.

The focusing optics 70 are suspended in weight-compensated manner on a mounting 78. The mounting 78 is indicated in FIG. 2 in greatly schematic manner by two vertical dashes drawn on either side of the focusing optics 70. The weight compensation of the focusing optics 70 is indicated schematically by a counterweight 80 which is connected to the focusing optics 70 via a rope/pulley arrangement 82 and which exerts a counterforce on the focusing optics 70 compensating the weight of said focusing optics. A rope/pulley arrangement is, of course, only one example of the attachment of a counterweight to the focusing optics. Alternatively, use could be made of a lever system, for example. Another possible configuration is shown in U.S. Pat. No. 5,336,215, where a spring system is used for the purpose of suspending focusing optics.

The focusing optics 70 are capable of being lowered, together with the mounting 78, in the vertical direction into the insertion funnel 20 of the suction-ring unit 16 seated on the eye 10 by a motorised, preferentially electromotive, drive unit 84, as indicated by the direction arrow 38. In this case the focusing optics 70 are not rigidly connected to the mounting 78 but possess in relation to the mounting 78 a certain capacity for displacement upwards contrary to the lowering direction 38. On account of the weight compensation of the focusing optics 70, a displacement of the same in relation to the mounting is already possible by virtue of an extremely small application of force. The moment at which the applanation plate 40 comes into contact with the eye and experiences a counterpressure from the eye may therefore already result in a displacement of the focusing optics 70 relative to the mounting 78. This displacement is detected by means of a limit switch 86 (alternatively, for example, a counterforce switch) which is fitted in stationary manner relative to the mounting 78 and which provides its switching signal to the control device 72. The switching of the limit switch 86 consequently signals to the control device 72 the attaining of the predetermined relative position between interface unit 34 and suction-ring unit 16 (e.g. touching of the insertion funnel 20 by the interface unit 34), in which the further motorised lowering movement of the focusing optics 70 has to be stopped. Accordingly, when the switching signal is received from the limit switch 86 the control device 72 controls the drive unit 84 in the sense of an operational stop. The previous lowering of the focusing optics 70 by the drive unit 84 can likewise be controlled by the control device 72 in accordance with the control program 74; alternatively it is conceivable that the operator initialises the lowering movement manually by means of a joystick connected to the control device 72, in which case when the aforementioned predetermined relative position between interface unit 34 and suction-ring unit 16 is attained the control device 72 cancels the precedence of the joystick and stops the operation of the drive unit 84 automatically.

On account of the presence of the limit switch 86, in this case a sensor fitted to components 16 or/and 34 may be dispensed with.

The laser device according to FIG. 2 furthermore includes two evacuation pumps 88, 56 which via suitable hose lines are connected to a pipe nipple 92 and 94, respectively, formed on the suction-ring unit 16. Evacuation channel 28 according to FIGS. 1a-1c leads into pipe nipple 92; evacuation pump 88 consequently serves for evacuating suction chamber 30. On the other hand, evacuation channel 54 leads into pipe nipple 94, on account of which evacuation pump 56 serves for evacuating the space 58 shown in FIGS. 1a-1c.

In the case of an already evacuated suction chamber 30, in the previously described coupling position of interface unit 34 and suction-ring unit 16 the evacuation pump 56 is actuated, in order to evacuate the space 58. This evacuation of the space 58 can be initiated automatically by the control device 72 by reason of the relative position, detected with the sensor 50, of the two units, or even arbitrarily by the physician by hand. It is also possible to control the evacuation of the space 58 by means of the switch 86.

The invention claimed is:

1. An apparatus, comprising:
a mechanical interface unit coupled to a suction-ring unit capable of being mounted onto an eye without the apparatus touching or applying a vacuum to a cornea of the eye to allow the cornea to receive laser radiation while free from contact;
the suction-ring unit defining a central opening and a ring axis, the suction-ring unit comprising:
a suction ring comprising:
a first evacuation channel; and
a first sealing surface and a second sealing surface each configured to contact a sclera of the eye such that the sclera, the first sealing surface, and the second sealing surface define a suction chamber that, when evacuated via the first evacuation channel, creates a first vacuum only in the suction chamber, the first vacuum coupling the suction-ring unit to the sclera of the eye such that the first vacuum is not applied to the cornea to allow the cornea to receive the laser radiation while free from contact; and
an insertion funnel comprising:
a second evacuation channel spaced from the first evacuation channel; and
a first ring seal and a second ring seal; and
the mechanical interface unit separate from the suction-ring unit and capable of being:
moved along the ring axis, at least partially into the central opening, and into coupling contact with the suction-ring unit,
mechanically coupled with optics configured to focus the laser radiation onto or into the cornea of the eye via the central opening of the suction-ring unit,
wherein:
when the mechanical interface unit is moved into coupling contact with the suction-ring unit, a space is formed by the first ring seal, the second ring seal, an outer surface of the mechanical interface unit, and an inner surface of the insertion funnel of the suction-ring unit;
the second evacuation channel of the suction-ring unit is configured to evacuate the space thereby creating a second vacuum only in the space such that the second vacuum is not applied to the cornea; and
the second vacuum couples the mechanical interface unit with the suction-ring unit such that the mechanical interface unit is exposed to the cornea through the central opening of the suction-ring unit, but does not touch the cornea to allow the cornea to receive the laser radiation while free from contact.

2. The apparatus of claim 1, wherein portions of the outer surface of the mechanical interface unit and the inner surface of the insertion funnel of the suction-ring unit defining the space are frustoconical.

3. The apparatus of claim 1, further comprising a sensor for detecting a relative position of the mechanical interface unit to the suction-ring unit.

4. The apparatus of claim 3, wherein the sensor is coupled to the suction-ring unit.

5. The apparatus of claim 3, wherein the sensor is coupled to the optics.

6. The apparatus of claim 3, wherein the sensor is a switch.

7. The apparatus of claim 1, further comprising a laser system including the optics.

8. The apparatus of claim 7, wherein the laser system includes at least one evacuation pump in communication with the first and second evacuation channels.

9. The apparatus of claim 8, wherein:
the at least one evacuation pump comprises at least two evacuation pumps;
a first of the at least two evacuation pumps is in communication with the first evacuation channel; and
a second of the at least two evacuation pumps is in communication with the second evacuation channel.

* * * * *